United States Patent
Arditty et al.

(10) Patent No.: US 10,154,954 B2
(45) Date of Patent: Dec. 18, 2018

(54) LIQUID COSMETIC COMPOSITION COMPRISING TWO ORGANOPOLYSILOXANE ELASTOMERS, A WAX AND A NON-VOLATILE OIL

(75) Inventors: Stephane Arditty, L'Hay les Roses (FR); Veronique Jacques, L'Hay les Roses (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/401,874

(22) PCT Filed: Jun. 6, 2012

(86) PCT No.: PCT/EP2012/060712
§ 371 (c)(1),
(2), (4) Date: Nov. 18, 2014

(87) PCT Pub. No.: WO2013/182238
PCT Pub. Date: Dec. 12, 2013

(65) Prior Publication Data
US 2015/0110884 A1    Apr. 23, 2015

(51) Int. Cl.
| | | |
|---|---|---|
| *A61K 8/89* | (2006.01) | |
| *A61K 8/92* | (2006.01) | |
| *A61Q 1/02* | (2006.01) | |
| *A61Q 19/00* | (2006.01) | |
| *A61Q 1/04* | (2006.01) | |
| *A61Q 1/06* | (2006.01) | |
| *A61K 8/02* | (2006.01) | |
| *A61K 8/895* | (2006.01) | |
| *A61K 8/891* | (2006.01) | |

(52) U.S. Cl.
CPC .............. *A61K 8/89* (2013.01); *A61K 8/0241* (2013.01); *A61K 8/891* (2013.01); *A61K 8/895* (2013.01); *A61K 8/92* (2013.01); *A61Q 1/02* (2013.01); *A61Q 1/04* (2013.01); *A61Q 1/06* (2013.01); *A61Q 19/00* (2013.01); *A61K 2800/31* (2013.01); *A61K 2800/43* (2013.01); *A61K 2800/436* (2013.01); *A61K 2800/624* (2013.01); *A61K 2800/654* (2013.01)

(58) Field of Classification Search
None
See application file for complete search history.

(56) References Cited

U.S. PATENT DOCUMENTS

2009/0053269 A1    2/2009  Shimizu
2009/0092567 A1*   4/2009  Chou .................. A61K 8/31
                                                        424/64

FOREIGN PATENT DOCUMENTS

CN    101151017 A    3/2008
FR    2 924 929 A1   6/2009

OTHER PUBLICATIONS

International Search Report dated Mar. 1, 2013, in PCT/EP2012/060712, filed Jun. 6, 2012.
Office Action dated Aug. 3, 2017 in Chinese Patent Application No. 201280073734.1 (with English translation).

* cited by examiner

*Primary Examiner* — Carlos A Azpuru
*Assistant Examiner* — Casey S Hagopian
(74) *Attorney, Agent, or Firm* — Oblon, McClelland, Maier & Neustadt, L.L.P.

(57) ABSTRACT

The present invention is an anhydrous cosmetic composition for making up and/or caring for the skin and/or lips, which is liquid at 20° C., comprising, in a physiologically acceptable medium, at least one fatty phase comprising: —at least one organopolysiloxane elastomer powder coated with silicone resin, —at least one organopolysiloxane elastomer conveyed in a first oil, —at least one wax, and —at least one second oil, —the said organopolysiloxane elastomer and the organopolysiloxane elastomer powder coated with a silicone resin being present in a ratio by weight on a dry basis of organopolysiloxane elastomer conveyed in an oil/organopolysiloxane elastomer powder coated with a silicone resin of greater than 2 and preferably of greater than 2.5.

21 Claims, No Drawings

LIQUID COSMETIC COMPOSITION COMPRISING TWO ORGANOPOLYSILOXANE ELASTOMERS, A WAX AND A NON-VOLATILE OIL

The present invention relates to a cosmetic composition for making up and/or caring for the skin and/or lips comprising at least one organopolysiloxane elastomer powder coated with silicone resin, an organopolysiloxane elastomer conveyed in a first oil, a wax, an organic lacquer and a second oil, the said elastomers being present in a specific ratio by weight.

The development of formulations devoted to making up and/or caring for the skin and/or lips, having satisfactory properties in terms of application, of comfort, which are in particular non-tacky, of hold and of coverage but also in terms of make-up effect, is an ongoing objective.

The lipstick, which appeared at the beginning of the last century, has become essential and is recognized by users as the overwhelmingly predominant method of application in making up their skin and in particular their lips. This method of application offers users a means of choice, in terms of coverage of the lips and diversity in the colours.

Compositions for making up the skin or lips in the form of fluids, conventionally referred to as glosses in the context of making up the lips, are also known, which are generally devoid of waxes and which conventionally comprise at least one nonvolatile oil with a molecular weight of greater than 600 g/mol.

However, the deposited layers produced with such compositions are generally relatively glossy and/or tacky and/or exhibit a feeling of greasiness on the lips, which is a source of discomfort to the user.

Solid make-up compositions in the foam form are also known, such as, for example, those described in Application US-2009-0092567. However, these compositions can prove to be difficult to apply homogeneously and the mattness of the deposited layers produced remains inadequate.

Thus, it would be advantageous to have available compositions for making up the skin and/or lips, in particular the lips, which are in the liquid form and which are capable of providing a matt result, having good coverage, which is homogeneous and non-tacky, in particular on the lips.

Likewise, consumers are on the lookout for such liquid formulations which can make it possible to generate a soft feeling on the lips, which might be described as "velvety" or "satiny".

Consequently, there remains at the current time a need to have available a cosmetic composition for making up and/or caring for the skin and/or lips, in particular of gloss type for the lips, which is in the liquid form and which has good comfort properties, in particular providing a soft "velvet" finish resembling a feeling of a powdery product on the lips, which is non-tacky, with a matt make-up result exhibiting a good level of coverage.

The inventors have found that a cosmetic composition comprising at least one organopolysiloxane elastomer powder coated with silicone resin, an organopolysiloxane elastomer conveyed in a first oil, preferably a non-volatile oil, a wax, an organic lacquer and a second oil, the said elastomers being present in a specific ratio by weight, makes it possible to obtain such a result.

Thus, the subject-matter of the present invention is mainly an anhydrous cosmetic composition for making up and/or caring for the skin and/or lips, which is liquid at 20° C., comprising, in a physiologically acceptable medium, at least one fatty phase comprising:

at least one organopolysiloxane elastomer powder coated with silicone resin,
at least one organopolysiloxane elastomer conveyed in a first oil,
at least one wax, and
at least one second oil,
the said organopolysiloxane elastomer and the organopolysiloxane elastomer powder coated with a silicone resin being present in a ratio by weight on a dry basis of organopolysiloxane elastomer conveyed in an oil/organopolysiloxane elastomer powder coated with a silicone resin of greater than 2 and preferably of greater than 2.5.

In particular, the invention relates to an anhydrous cosmetic composition for making up and/or caring for the skin and/or lips, which is liquid at 20° C., comprising, in a physiologically acceptable medium, at least one fatty phase comprising:

at least one organopolysiloxane elastomer powder coated with silicone resin,
at least one organopolysiloxane elastomer conveyed in a first oil,
at least one wax,
at least one second oil, and
the said organopolysiloxane elastomer and the organopolysiloxane elastomer powder coated with a silicone resin being present in a ratio by weight on a dry basis of organopolysiloxane elastomer conveyed in an oil/organopolysiloxane elastomer powder coated with a silicone resin of greater than 2 and preferably of greater than 2.5,
with the exception of the following liquid lipstick compositions 1 and 2:

| Compounds | Composition 1 (% by weight) | Composition 2 (% by weight) |
|---|---|---|
| BHT | 0.03 | 0.03 |
| Kaolin | 5 | 5 |
| Silica Dimethyl Silylate (Aerosil ® R 972 from Evonik Degussa) | 2 | 2 |
| Red 7 lake | 3.83 | 3.83 |
| Red 28 lake | 1.17 | 1.17 |
| Iron oxides | 1 | 1 |
| Bis-Diglyceryl Polyacyladipate-2 (Softisan ® 649 from Sasol) | q.s. for 100 | q.s. for 100 |
| Isostearyl isostearate | 3.9 | 3.9 |
| Tridecyl trimellitate | 7.3 | 7.3 |
| Ozokerite (Ozokerite Wax Pastilles SP 1021 P from Strahl & Pitsch) | — | 1.3 |
| Hydrogenated polyisobutene (Parleam ® from Nof Corporation) | 8.6 | 8.6 |
| Polyethylene (Asensa ® SC 211 from Honeywell) | 1.2 | 1.2 |
| Polyethylene (Performalene 500-L polyethylene from New Phase Technologies) | 1 | — |
| Nylon-12 (SP - 500 from Toray (Dow Corning)) | 1.5 | 1.5 |
| Phenyl Trimethicone (Dow Corning 556 Cosmetic Grade Fluid from Dow Corning) | 7.8 | 7.8 |
| Vinyl Dimethicone/Methicone Silsesquioxane Crosspolymer (KSP 100 from Shin Etsu) | 2 | 2 |
| Dimethicone (and) Dimethicone Crosspolymer (Dow Corning 9041 Silicone Elastomer Blend from Dow Corning) comprising 15.5% of elastomer in dimethicone | 33 | 33 |
| TOTAL | 100 | 100 |

In a composition according to the invention as defined above, the organopolysiloxane elastomer is conveyed in a first oil, preferably a non-volatile oil, in particular in the form of an organopolysiloxane elastomer gel.

Preferably, the composition according to the invention is intended for making up and/or caring for the lips.

Preferably, the composition according to the invention is a liquid (in contrast to solid) lipstick conventionally referred to as a gloss.

The composition according to the invention is easy to apply and makes it possible to obtain a deposited layer on the lips which is satisfactory in terms of coverage, is matt (non-glossy) and which confers, on the lips, a "velvet" feeling, that is to say a soft and velvety feeling, without a feeling of tackiness.

Preferably, according to some embodiments, it is desirable to obtain a composition for which the make-up result is homogeneous and does not bring about a feeling of tightness or drying of the lips.

The invention also relates to a cosmetic method for caring for and/or making up the skin and/or lips, comprising the application, to the skin and/or lips, of a composition as defined above.

The invention also relates to the use of a composition as defined above for obtaining a matt (that is to say, non-glossy) make-up of the skin and/or lips, preferably of the lips.

Within the meaning of the present invention, "liquid" (may also be referred to as "fluid"), in contrast to "solid", is intended to describe any composition capable of matching the shape of its container, at ambient temperature (20° C.).

More specifically, a liquid composition according to the invention can in particular be characterized by a viscosity value at ambient temperature (20° C.).

Preferably, the composition exhibits, at 20° C., a viscosity varying from 1 to 25 Pa·s. Particularly preferably, the viscosity of the composition varies between 5 and 20 Pa·s and better still between 7 and 16 Pa·s.

More preferably, the composition exhibits, at 20° C., a viscosity varying from 10 to 13 Pa·s.

Protocol for Measuring the Viscosity

The viscosity measurement is generally performed at 20° C., using a Rheomat RM180 viscometer equipped with a No. 4 spindle, the measurement being performed after 10 minutes of rotation of the spindle in the composition (after which time stabilization of the viscosity is observed) at a rate of 200 revolutions/min.

Physiologically Acceptable Medium

The term "physiologically acceptable medium" is intended to denote a medium which is particularly suitable for the application of a composition of the invention to the skin and/or lips.

The physiologically acceptable medium is generally adapted to the nature of the support onto which the composition has to be applied, and also to the appearance under which the composition has to be packaged.

The term "anhydrous" especially means that water is preferably not deliberately added to the compositions, but may be present in trace amounts in the various compounds used in the compositions.

Organopolysiloxane Elastomer Powder Coated with Silicone Resin

The composition according to the invention comprises at least one organopolysiloxane elastomer powder coated with silicone resin, in particular silsesquioxane resin, as described, for example, in U.S. Pat. No. 5,538,793, the content of which is incorporated by way of reference.

Such elastomeric powders are sold under the names KSP-100, KSP-101, KSP-102, KSP-103, KSP-104 and KSP-105 by the company Shin-Etsu, and have the INCI name: Vinyl Dimethicone/Methicone Silsesquioxane Crosspolymer.

Preferably, the organopolysiloxane elastomer powder coated with silicone resin is a compound having the INCI name: Vinyl Dimethicone/Methicone Silsesquioxane Crosspolymer.

Preferably, the composition according to the invention comprises an organopolysiloxane elastomer powder coated with silicone resin, in particular with silsesquioxane resin, in a total content ranging from 0.5% to 20% by weight, relative to the total weight of the composition, in particular from 0.5% to 10% by weight and preferably from 1% to 5% by weight, relative to the total weight of the composition.

Organopolysiloxane Elastomer Conveyed in an Oil

The composition according to the invention comprises, in addition to the organopolysiloxane elastomer powder coated with silicone resin, at least one organopolysiloxane elastomer (also referred to as silicone elastomer) conveyed in a first oil, in particular in the form of an organopolysiloxane elastomer gel.

Preferably, the said oil is a silicone oil and/or a hydrocarbon oil, which is preferably non-volatile.

Preferably, the said composition comprises at least one organopolysiloxane elastomer conveyed in at least one non-volatile silicone oil having the INCI name Dimethicone.

The term "organopolysiloxane elastomer" or "silicone elastomer" means a soft, deformable organopolysiloxane with viscoelastic properties and especially with the consistency of a sponge or soft sphere. Its modulus of elasticity is such that this material withstands deformation and has a limited capacity for extension and contraction. This material is capable of regaining its original shape after stretching.

It is more particularly a crosslinked silicone elastomer.

The silicone elastomer particles are conveyed in the form of a gel formed from an elastomeric organopolysiloxane included in at least one hydrocarbon oil and/or one silicone oil.

In these gels, the organopolysiloxane particles are often non-spherical particles.

Non-Emulsifying Organopolysiloxane Elastomer

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysiloxane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst.

In particular, the organopolysiloxane elastomer may be obtained by reaction of dimethylpolysiloxane containing dimethylvinylsiloxy end groups and of methylhydrogenopolysiloxane containing trimethylsiloxy end groups, in the presence of a platinum catalyst.

Compound (A) is the base reactant for the formation of elastomeric organopolysiloxane, and the crosslinking takes place via an addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon groups such as an epoxy group, a carboxylate ester group or a mercapto group.

Compound (A) may thus be chosen from methylhydrogenopolysiloxanes containing trimethylsiloxy end groups, dimethylsiloxane-methylhydrogenosiloxane copolymers containing trimethylsiloxy end groups, and dimethylsiloxane-methylhydrogenosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located in any position of the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon groups such as an epoxy group, a carboxylate ester group or a mercapto group.

The organopolysiloxanes (B) may be chosen from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

In particular, the organopolysiloxane elastomer may be obtained by reaction of dimethylpolysiloxane containing dimethylvinylsiloxy end groups and of methylhydrogenopolysiloxane containing trimethylsiloxy end groups, in the presence of a platinum catalyst.

According to another alternative form, compound (B) may be an unsaturated hydrocarbon compound containing at least two lower alkenyl groups (for example $C_2$-$C_4$); the lower alkenyl group may be chosen from vinyl, allyl and propenyl groups. These lower alkenyl groups may be located in any position of the molecule, but are preferably located at the ends. By way of example, mention may be made of hexadiene, in particular of 1,5-hexadiene.

Advantageously, the sum of the number of ethylenic groups per molecule in compound (B) and of the number of hydrogen atoms bonded to silicon atoms per molecule in compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units.

The organopolysiloxane elastomer particles are preferably conveyed in the form of a gel formed from an elastomeric organopolysiloxane included in at least one hydrocarbon oil and/or one silicone oil, as defined below. In these gels, the organopolysiloxane particles may be spherical or non-spherical particles.

Spherical non-emulsifying elastomers that may be used include, for example, those sold under the names DC 9040, DC 9041, DC 9509, DC 9505 by the company Dow Corning.

Use may also be made of those sold under the names KSG-6, KSG-15, KSG-16, KSG-18, KSG-41, KSG-42, KSG-43 and KSG-44 by the company Shin-Etsu; Gransil SR 5CYC Gel, Gransil SR DMF 10 Gel and Gransil SR DC556 Gel from the company Gransil RPS from Grant Industries; 1229-02-167, 1229-02-168 and SFE 839 from the company General Electric.

According to a preferred embodiment, the composition according to the invention comprises, as organopolysiloxane elastomer conveyed in an oil, a non-emulsifying elastomer, preferably spherical, preferably chosen from the compounds sold under the names DC 9040, DC 9041, DC 9509, DC 9505 by the company Dow Corning.

According to one particular embodiment, elastomers may be used as a mixture with a cyclic silicone oil. An example that may be mentioned is the mixture of crosslinked organopolysiloxane/cyclopentasiloxane or a mixture of crosslinked organopolysiloxane/cyclohexasiloxane, for instance Gransil RPS D5 or Gransil RPS D6 from the company Grant Industries.

Emulsifying Organopolysiloxane Elastomer

According to another embodiment, the composition according to the invention comprises, as organopolysiloxane elastomer conveyed in an oil, an emulsifying elastomer.

The term "emulsifying organopolysiloxane elastomer" means an organopolysiloxane elastomer comprising at least one hydrophilic chain, such as polyoxyalkylenated organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained by crosslinking addition reaction of diorganopolysiloxane containing at least one hydrogen bonded to silicon and of a polyoxyalkylene containing at least two ethylenically unsaturated groups.

Preferably, the polyoxyalkylenated organopolysiloxane elastomer is obtained by crosslinking addition reaction (A1) of diorganopolysiloxane containing at least two hydrogens each bonded to a silicon, and (B1) of polyoxyalkylene containing at least two ethylenically unsaturated groups, especially in the presence (C1) of a platinum catalyst, as described, for instance, in U.S. Pat. No. 5,236,986 and U.S. Pat. No. 5,412,004.

In particular, the organopolysiloxane may be obtained by reaction of polyoxyalkylene (especially polyoxyethylene and/or polyoxypropylene) containing dimethylvinylsiloxy end groups and of methylhydrogenopolysiloxane containing trimethylsiloxy end groups, in the presence of a platinum catalyst.

The organic groups bonded to the silicon atoms of compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenylethyl; and substituted monovalent hydrocarbon groups such as an epoxy group, a carboxylate ester group or a mercapto group.

Compound (A1) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, dimethylsiloxane-methylhydrogenosiloxane-laurylmethylsiloxane copolymers containing trimethylsiloxy end groups.

Compound (C1) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated organopolysiloxane elastomers may be formed from divinyl compounds, in particular polyoxyalkylenes containing at least two vinyl groups, which react with Si—H bonds of a polysiloxane.

Polyoxyalkylenated elastomers are especially described in U.S. Pat. No. 5,236,986, U.S. Pat. No. 5,412,004, U.S. Pat. No. 5,837,793 and U.S. Pat. No. 5,811,487, the content of which is incorporated by reference.

Polyoxyalkylenated organopolysiloxane elastomers that may be used include those sold under the names KSG-21, KSG-20, KSG-30, KSG-31, KSG-32, KSG-33, KSG-210, KSG-310, KSG-320, KSG-330 and KSG-340 by the company Shin-Etsu, and DC9010 and DC9011 by the company Dow Corning.

The emulsifying organopolysiloxane elastomer may also be chosen from polyglycerolated organopolysiloxane elastomers.

The polyglycerolated organopolysiloxane elastomer according to the invention is an organopolysiloxane elastomer that may be obtained by crosslinking addition reaction of diorganopolysiloxane containing at least one hydrogen bonded to silicon and of polyglycerolated compounds containing ethylenically unsaturated groups, especially in the presence of a platinum catalyst.

Preferably, the organopolysiloxane elastomer is obtained by crosslinking addition reaction (A2) of diorganopolysiloxane containing at least two hydrogens each bonded to a silicon, and (B2) of glycerolated compounds containing at least two ethylenically unsaturated groups, especially in the presence (C2) of a platinum catalyst.

In particular, the organopolysiloxane may be obtained by reaction of a polyglycerolated compound containing dimethylvinylsiloxy end groups and of methylhydrogenopolysiloxane containing trimethylsiloxy end groups, in the presence of a platinum catalyst.

Compound (A2) is the base reactant for the formation of an organopolysiloxane elastomer, and the crosslinking is performed by addition reaction of compound (A2) with compound (B2) in the presence of the catalyst (C2).

Compound (A2) is in particular an organopolysiloxane containing at least two hydrogen atoms bonded to different silicon atoms in each molecule.

Compound (A2) may have any molecular structure, especially a linear-chain or branched-chain structure or a cyclic structure.

Compound (A2) may have a viscosity at 25° C. ranging from 1 to 50 000 centistokes, especially so as to be miscible with compound (B2).

The organic groups bonded to the silicon atoms in compound (A2) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon groups such as an epoxy group, a carboxylate ester group or a mercapto group.

Preferably, the said organic group is chosen from methyl, phenyl and lauryl groups.

Compound (A2) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers and dimethylsiloxane-methylhydrogenosiloxane-laurylmethylsiloxane copolymers containing trimethylsiloxy end groups.

Compound (B2) may be a polyglycerolated compound corresponding to formula (B') below:

$$C_mH_{2m-1}\text{—O-[Gly]}_n\text{-}C_mH_{2m-1} \quad (B')$$

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferentially ranging from 2 to 5, and in particular n is equal to 3; Gly denotes:

—CH$_2$—CH(OH)—CH$_2$—O— or

—CH$_2$—CH(CH$_2$OH)—O—

Advantageously, the sum of the number of ethylenic groups per molecule in compound (B2) and of the number of hydrogen atoms bonded to silicon atoms per molecule in compound (A2) is at least 4.

It is advantageous for compound (A2) to be added in an amount such that the molecular ratio between the total amount of hydrogen atoms bonded to silicon atoms in compound (A2) and the total amount of all the ethylenically unsaturated groups in compound (B2) is within the range from 1/1 to 20/1.

Compound (C2) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in an amount of from 0.1 to 1000 parts by weight and better still from 1 to 100 parts by weight, as clean platinum metal, per 1000 parts by weight of the total amount of compounds (A2) and (B2).

The polyglycerolated organopolysiloxane elastomer is conveyed in gel form in at least one hydrocarbon oil and/or one silicone oil. In these gels, the polyglycerolated elastomer is often in the form of non-spherical particles.

Polyglycerolated organopolysiloxane elastomers that may be used include those sold under the names KSG-710, KSG-810, KSG-820, KSG-830 and KSG-840 by the company Shin-Etsu.

Preferably, the silicone elastomer conveyed in a first oil is non-emulsifying and is preferably devoid of a hydrophilic chain and in particular devoid of polyoxyalkylene units and polyglyceryl units.

Advantageously, the organopolysiloxane elastomer under consideration according to the invention is chosen from spherical non-emulsifying organopolysiloxane elastomers, polyglycerolated organopolysiloxane elastomers and polyoxyalkylenated organopolysiloxane elastomers.

Advantageously, the organopolysiloxane elastomer under consideration according to the invention is chosen from spherical non-emulsifying organopolysiloxane elastomers.

More particularly, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence of a platinum catalyst (C).

The composition thus comprises an organopolysiloxane elastomer conveyed in a non-volatile oil in combination with at least one organopolysiloxane elastomer powder coated with a silicone resin.

Advantageously, the composition according to the invention comprises a content of organopolysiloxane elastomer(s) conveyed in an oil in a total solids content ranging from 0.5% to 20% by weight, preferably from 0.5% to 10% by weight and more preferably still from 1% to 8% by weight, relative to the total weight of the composition.

In the composition according to the invention, the said organopolysiloxane elastomer(s) and the organopolysiloxane elastomer(s) powder coated with a silicone resin are present in a ratio by weight on a dry basis of organopolysiloxane elastomer(s) conveyed in an oil (i.e., the total solids content of organopolysiloxane elastomer(s) conveyed in an oil)/organopolysiloxane elastomer(s) powder coated with a silicone resin (i.e., the total content of organopolysiloxane elastomer(s) coated with a silicone resin) of greater than 2, preferably of greater than 2.5.

The organopolysiloxane elastomer(s) conveyed in an oil and the organopolysiloxane elastomer(s) powder coated with a silicone resin can be present in a ratio by weight on a dry basis of organopolysiloxane elastomer conveyed in an oil/organopolysiloxane elastomer powder coated with a silicone resin of between 2 and 10, preferably between 2 and 8 and more preferably still between 2.5 and 5.

Advantageously, the composition according to the invention comprises a total content of organopolysiloxane elastomer(s) (i.e., =of elastomer(s) conveyed in an oil or not conveyed in an oil+organopolysiloxane elastomer coated with silicone resin solids) ranging from 1% to 25% by weight, preferably from 2% to 15% by weight and more preferably still from 5% to 15% by weight, relative to the total weight of the composition.

Advantageously, the composition according to the invention comprises a total content of organopolysiloxane elastomer(s) (i.e., =of elastomer(s) conveyed in an oil or not conveyed in an oil+organopolysiloxane elastomer coated with silicone resin solids) of greater than 5%, relative to the total weight of the composition, preferably ranging from 5% to 15% by weight, preferably ranging from 5% to 10% by weight, relative to the total weight of the composition.

The combination of these elastomers in this specific ratio by weight makes it possible to obtain a deposited layer on the skin and/or lips which is homogeneous, matt and non-tacky and which also exhibits a velvety and soft feeling.

Wax

As stated above, a composition according to the invention comprises at least one wax.

The term "wax" is understood, within the meaning of the present invention, to mean a lipophilic compound, which is solid at ambient temperature (25° C.), with a reversible solid/liquid change in state, and which has a melting point of greater than or equal to 30° C. which can range up to 120° C.

The melting point of the wax may be measured using a differential scanning calorimeter (DSC), for example the calorimeter sold under the name DSC 30 by the company Mettler.

Preferably, the measuring protocol is as follows:

A sample of 5 mg of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the value of the temperature corresponding to the tip of the peak of the curve representing the variation in the difference in power absorbed as a function of the temperature.

The wax may especially have a hardness ranging from 0.05 MPa to 15 MPa and preferably ranging from 6 MPa to 15 MPa. The hardness is determined by measuring the compressive force, measured at 20° C. using the texture analyser sold under the name TA-TX2i by the company Rheo, equipped with a stainless-steel cylinder with a diameter of 2 mm, travelling at a measuring speed of 0.1 mm/second, and penetrating the wax to a penetration depth of 0.3 mm.

The waxes may be hydrocarbon waxes or fluoro waxes, and may be of vegetable, mineral, animal and/or synthetic origin.

In particular, the waxes have a melting point of greater than 25° C. and better still of greater than 45° C.

Preferably, the composition according to the invention comprises a wax content of between 0.5% and 10% by weight and preferably between 0.5% and 8% by weight, relative to the total weight of the composition.

Preferably, the composition according to the invention comprises a wax content of between 1% and 5%.

Non-Polar Wax

Preferably, the composition according to the invention comprises at least one non-polar wax.

Within the meaning of the present invention, the term "non-polar wax" means a wax for which the solubility parameter $\delta_a$ at 25° C. as defined below is equal to 0 $(J/cm^3)^{1/2}$.

Non-polar waxes are in particular hydrocarbon waxes composed solely of carbon and hydrogen atoms and devoid of heteroatoms, such as N, O, Si and P.

In particular, non-polar wax is understood to mean a wax which is composed solely of non-polar wax.

Preferably, it is not a mixture comprising other types of waxes which are not non-polar waxes.

As illustrations of non-polar waxes that are suitable for the invention, mention may be made especially of hydrocarbon waxes, for instance microcrystalline waxes, paraffin waxes, ozokerite and polyethylene waxes.

According to a preferred embodiment, a composition in accordance with the invention comprises ozokerite.

Mention may in particular be made, as ozokerite, of that sold under the name Ozokerite Wax Pastilles SP 1021 P.

According to a preferred embodiment, a composition in accordance with the invention comprises a polyethylene wax.

Polyethylene waxes that may be mentioned include Asensa® SC 211 sold by Honeywell, and Performalene 500-L Polyethylene and Performalene 400 Polyethylene sold by New Phase Technologies.

According to a preferred embodiment, a composition in accordance with the invention comprises ozokerite and a polyethylene wax.

As microcrystalline waxes that may be used, mention may be made of Multiwax W 445® sold by the company Sonneborn, and Microwax HW® and Base Wax 30540® sold by the company Paramelt.

As microwaxes that may be used in the compositions according to the invention as non-polar wax, mention may be made especially of polyethylene microwaxes such as those sold under the names Micropoly 200®, 220®, 220L® and 250S® by the company Micro Powders.

Preferably, the composition according to the invention has a non-polar wax content of between 0.5% and 10% by weight and preferably between 0.5% and 8% by weight, relative to the total weight of the composition.

Preferably, the composition according to the invention has a non-polar wax content of between 1% and 5% by weight, relative to the total weight of the composition.

Polar Wax

According to one embodiment, the composition according to the invention may comprise at least one polar wax.

Within the meaning of the present invention, the term "polar wax" means a wax for which the solubility parameter $\delta_a$ at 25° C. is other than 0 $(J/cm^3)^{1/2}$.

In particular, the term "polar wax" means a wax whose chemical structure is formed essentially from, or even composed of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: "*The three-dimensional solubility parameters*", J. Paint Technol., 39, 105 (1967).

According to this Hansen space:
- $\delta_D$ characterizes the London dispersion forces derived from the formation of dipoles induced during molecular impacts;
- $\delta_p$ characterizes the Debye interaction forces between permanent dipoles and also the Keesom interaction forces between induced dipoles and permanent dipoles;
- $\delta_h$ characterizes the forces of specific interactions (such as acid/base, donor/acceptor, hydrogen bonds, etc.); and
- $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

The polar waxes may especially be hydrocarbon, fluoro or silicone waxes.

Preferentially, the polar waxes may be hydrocarbon waxes or fluoro waxes.

The term "silicone wax" means a wax comprising at least one silicon atom, especially comprising Si—O groups.

The term "hydrocarbon wax" means a wax formed essentially from, or even composed of, carbon and hydrogen atoms, and optionally oxygen and nitrogen atoms, and that does not contain any silicon or fluorine atoms. It may contain alcohol, ester, ether, carboxylic acid, amine and/or amide groups.

According to a first preferred embodiment, the polar wax is a hydrocarbon wax.

As a hydrocarbon polar wax, a wax chosen from ester waxes and alcohol waxes is in particular preferred.

The expression "ester wax" is understood according to the invention to mean a wax comprising at least one ester functional group.

According to the invention, the term "alcohol wax" means a wax comprising at least one alcohol functional group, i.e. comprising at least one free hydroxyl (OH) group.

The following may especially be used as ester wax:

ester waxes such as those chosen from:

i) Waxes of formula $R_1COOR_2$ in which $R_1$ and $R_2$ represent linear, branched or cyclic aliphatic chains, the number of atoms of which varies from 10 to 50, which may contain a heteroatom such as O, N or P and the melting point of which varies from 25° C. to 120° C. In particular, use may be made, as an ester wax, of a $C_{20}$-$C_{40}$ alkyl (hydroxystearyloxy)stearate (the alkyl group comprising from 20 to 40 carbon atoms), alone or as a mixture, or a $C_{20}$-$C_{40}$ alkyl stearate. Such waxes are especially sold under the names Kester Wax K 82 P®, Hydroxypolyester K 82 P®, Kester Wax K 80 P® or Kester Wax K82H by the company Koster Keunen.

Use may also be made of a glycol and butylene glycol montanate (octacosanoate) such as the wax Licowax KPS Flakes (INCI name: Glycol Montanate) sold by the company Clariant.

ii) Bis(1,1,1-trimethylolpropane) tetrastearate, sold under the name Hest 2T-4S® by the company Heterene.

iii) Diester waxes of a dicarboxylic acid of general formula $R^3$—(—OCO—$R^4$—COO—$R^5$), in which $R^3$ and $R^5$ are identical or different, preferably identical, and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturated groups. Preferably, the $C_4$-$C_{30}$ aliphatic group is linear and unsaturated.

iv) Mention may also be made of the waxes obtained by catalytic hydrogenation of animal or vegetable oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax Ricin 16L64® and 22L73® by the company Sophim. Such waxes are described in Application FR-A-2 792 190. Mention may be made, as waxes obtained by hydrogenation of olive oil esterified with stearyl alcohol, of those sold under the name Phytowax Olive 18 L 57.

v) Mention may also be made of beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax, montan wax, orange wax, laurel wax and hydrogenated jojoba wax.

According to a preferred embodiment, a composition in accordance with the invention comprises candelilla wax.

According to another embodiment, the polar wax may be an alcohol wax.

Alcohol waxes that may be mentioned include for example the wax Performacol 550-L Alcohol from New Phase Technologies, stearyl alcohol and cetyl alcohol.

According to a second embodiment, the polar wax may be a silicone wax, for instance siliconized beeswax.

Preferably, the composition according to the invention has a polar wax content, in particular a polar hydrocarbon wax content, of between 0.5% and 10% by weight and preferably between 0.5% and 8% by weight, relative to the total weight of the composition.

Preferably, the composition according to the invention has a polar wax content, in particular a polar hydrocarbon wax content, of between 1% and 5% by weight, relative to the total weight of the composition.

According to a preferred embodiment, a composition in accordance with the invention is devoid of silicone wax.

According to a particularly preferred embodiment, a composition in accordance with the invention comprises at least one non-polar hydrocarbon wax preferably chosen from microcrystalline waxes, paraffin waxes, ozokerite, polyethylene waxes and their mixtures.

Liquid Fatty Phase

The composition according to the invention comprises at least one fatty phase, in particular at least one first oil, conveying an organpolysiloxane elastomer, and at least one second oil.

The oil(s) may be chosen from volatile oils and/or non-volatile oils, or mixtures thereof.

The term "oil" means a water-immiscible non-aqueous compound that is liquid at ambient temperature (25° C.) and at atmospheric pressure (760 mmHg).

In particular, the first oil and the said second oil may be chosen from hydrocarbon oils, silicone oils and/or fluoro oils.

Preferentially, the first oil conveying the organopolysiloxane elastomer is chosen from volatile oils, preferably volatile silicone oils.

Preferentially, the second oil conveying the organopolysiloxane elastomer is chosen from non-volatile oils, preferably non-volatile hydrocarbon oils.

Volatile Oils

In particular, preferably, the said first oil in which the organopolysiloxane elastomer is conveyed is volatile.

Within the meaning of the present invention, the term "volatile oil" means an oil (or non-aqueous medium) capable of evaporating on contact with the skin in less than one hour, at ambient temperature and at atmospheric pressure. The volatile oil is a volatile cosmetic oil, which is liquid at ambient temperature, especially having a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

a. Silicone Oils

According to an alternative form of the invention, the volatile oil is a volatile silicone oil.

The term "silicone oil" means an oil comprising at least one silicon atom, especially comprising Si—O groups.

The volatile silicone oil that may be used in the invention may be chosen from silicone oils especially having a viscosity ≤8 centistokes (cSt) ($8 \times 10^{-6}$ m$^2$/s).

Use may in particular be made, as volatile oils, of those having a viscosity ≤8 centistokes ($8 \times 10^{-6}$ m$^2$/s) and having in particular from 2 to 10 silicon atoms and especially from 2 to 7 silicon atoms, these silicones optionally comprising alkyl or alkoxy groups having from 1 to 10 carbon atoms. The volatile silicone oil which can be used in the invention can be chosen from silicone oils having a flash point ranging from 40° C. to 102° C., preferably having a flash point of greater than 55° C. and less than or equal to 95° C. and preferably ranging from 65° C. to 95° C.

The volatile silicone oil may be chosen from linear or cyclic silicone oils, such as linear or cyclic polydimethylsiloxanes (PDMSs) containing from 3 to 7 silicon atoms.

Examples of such oils that may be mentioned include octyl trimethicone, hexyl trimethicone, decamethylcyclopentasiloxane (cyclopentasiloxane or D5), octamethylcyclotetrasiloxane (cyclotetradimethylsiloxane or D4), dodecamethylcyclohexasiloxane (D6), decamethyltetrasiloxane (L4), KF 96 A from Shin-Etsu, and polydimethylsiloxanes such as those sold under the references DC 200 (1.5 cSt), DC 200 (5 cSt) and DC 200 (3 cSt) by Dow Corning.

As volatile silicone oil that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

A composition according to the invention can comprise at least one volatile oil in a content of between 2% and 50% by weight, in particular of between 5% and 45% by weight, preferably of between 10% and 40% by weight and more particularly of between 15% and 40% by weight, with respect to the total weight of the composition.

Preferably, the composition comprises at least one volatile silicone oil, preferably chosen from dimethicones 5 and 6 cSt.

In particular, according to a preferred embodiment, the volatile oil present in the composition can correspond to the first oil in which the organopolysiloxane elastomer is conveyed.

According to a specific embodiment, the composition according to the invention can additionally comprise at least one additional volatile oil, other than the said first oil conveying the organopolysiloxane elastomer, which can thus correspond to the said second oil, or to an additional oil.

b. Hydrocarbon Oils

According to an alternative form of the invention, the volatile oil is a volatile hydrocarbon oil.

The term "hydrocarbon oil" means an oil formed essentially from, indeed even composed of, carbon and hydrogen atoms, and optionally oxygen and nitrogen atoms, and not containing any silicon or fluorine atoms. It may contain alcohol, ester, ether, carboxylic acid, amine and/or amide groups.

The volatile hydrocarbon oils (also known as solvents) can be chosen from hydrocarbon oils having from 8 to 16 carbon atoms (preferably between 8 and 14 carbon atoms) and in particular volatile hydrocarbon oils for which the flash point is less than or equal to 80° C. (the flash point is in particular measured according to Standard ISO 3679) and in particular:

- branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl,
- linear alkanes, for example such as n-dodecane ($C_{12}$) and n-tetradecane ($C_{14}$) sold by Sasol under the references, respectively, Parafol 12-97 and Parafol 14-97, and also mixtures thereof, the undecane-tridecane mixture, mixtures of n-undecane ($C_{11}$) and of n-tridecane ($C_{13}$) obtained in Examples 1 and 2 of Application WO2008/155059 from the company Cognis, and mixtures thereof,
- branched $C_8$-$C_{16}$ esters, isohexyl neopentanoate, and their mixtures. Other volatile hydrocarbon oils, for instance petroleum distillates, especially those sold under the name Shell Solt by the company Shell, may also be used. The volatile solvent is preferably chosen from volatile hydrocarbon oils containing from 8 to 16 carbon atoms, and mixtures thereof.

As other volatile hydrocarbon solvents (oils) that may be used in the composition according to the invention, mention may also be made of ketones that are liquid at ambient temperature, such as methyl ethyl ketone or acetone; short-chain esters (containing from 3 to 8 carbon atoms in total) such as ethyl acetate, methyl acetate, propyl acetate or n-butyl acetate; ethers that are liquid at ambient temperature, such as diethyl ether, dimethyl ether or dichlorodiethyl ether; alcohols and especially linear or branched lower monoalcohols containing from 2 to 5 carbon atoms, such as ethanol, isopropanol or n-propanol.

c. Fluoro Oils

The volatile oil may also be chosen from fluoro oils such as perfluoropolyethers, perfluoroalkanes, for instance perfluorodecalin, perfluoroadamantanes, perfluoroalkyl phosphate monoesters, diesters and triesters, and fluoro ester oils.

Volatile fluoro oils such as nonafluoromethoxybutane or perfluoromethylcyclopentane, and mixtures thereof, may also be used.

Non-Volatile Oil

Preferably, the composition according to the invention comprises at least one non-volatile oil. In particular, preferably, the said second oil is non-volatile.

The term "non-volatile" oil refers to an oil for which the vapour pressure at ambient temperature and atmospheric pressure is non-zero and less than 0.02 mmHg (2.66 Pa) and better still less than $10^{-3}$ mmHg (0.13 Pa).

The non-volatile oils may be hydrocarbon oils especially of vegetable origin, oils of synthetic or mineral origin, silicone oils, fluoro oils, or mixtures thereof.

Non-Polar Oil

According to a first embodiment, the said non-volatile oil may be a non-polar oil, preferably a non-polar hydrocarbon oil.

These oils may be of vegetable, mineral or synthetic origin.

Within the meaning of the present invention, the term "non-polar oil" means an oil for which the solubility parameter at 25° C., $\delta_a$, as defined above, is equal to 0 $(J/cm^3)^{1/2}$.

The term "hydrocarbon oil" means an oil formed essentially from, indeed even composed of, carbon and hydrogen atoms, and optionally oxygen and nitrogen atoms, and not containing any silicon or fluorine atoms. It may contain alcohol, ester, ether, carboxylic acid, amine and/or amide groups.

Preferably, the non-volatile non-polar hydrocarbon oil may be chosen from linear or branched hydrocarbons of mineral or synthetic origin, such as:

- liquid paraffin or derivatives thereof,
- squalane,
- isoeicosane,
- naphthalene oil,
- polybutylenes such as Indopol H-100 (molar mass or MW=965 g/mol), Indopol H-300 (MW=1340 g/mol) and Indopol H-1500 (MW=2160 g/mol) sold or manufactured by the company Amoco,
- hydrogenated polyisobutylenes such as Parleam® sold by the company Nippon Oil Fats Corporation, Panalane H-300 E sold or manufactured by the company Amoco (MW=1340 g/mol), Viseal 20000 sold or manufactured by the company Synteal (MW=6000 g/mol) or Rewopal PIB 1000 sold or manufactured by the company Witco (MW=1000 g/mol),
- decene/butene copolymers, polybutene/polyisobutene copolymers, especially Indopol L-14,
- polydecenes and hydrogenated polydecenes such as: Puresyn 10 (MW=723 g/mol) and Puresyn 150 (MW=9200 g/mol) sold or manufactured by the company Mobil Chemicals,
- and mixtures thereof.

Preferably, the composition according to the invention comprises at least one non-polar oil preferably chosen from hydrogenated polyisobutenes and/or polybutenes.

Polar Oil

According to a particular embodiment, the composition comprises at least one non-volatile polar oil. The said oil may be a hydrocarbon oil, silicone oil or fluoro oil.

Preferentially, the said non-volatile oil is a polar hydrocarbon oil.

The term "silicone oil" means an oil containing at least one silicon atom, and especially containing Si—O groups.

The term "fluoro oil" means an oil containing at least one fluorine atom.

These oils may be of vegetable, mineral or synthetic origin.

Within the meaning of the present invention, the term "polar oil" means an oil for which the solubility parameter at 25° C., $\delta_a$, is other than 0 $(J/cm^3)^{1/2}$.

In particular, the non-volatile polar hydrocarbon oil may be chosen from the list of oils below, and mixtures thereof:

- hydrocarbon vegetable oils such as liquid triglycerides of fatty acids containing from 4 to 10 carbon atoms, for instance heptanoic or octanoic acid triglycerides or jojoba oil;
- ester oils, preferably chosen from:
  - fatty acid esters, in particular of 4 to 22 carbon atoms, and especially of octanoic acid, heptanoic acid, lanolic acid, oleic acid, lauric acid or stearic acid, for instance propylene glycol dioctanoate, propylene glycol monoisostearate or neopentyl glycol diheptanoate, synthetic esters, for instance the oils of formula $R_1COOR_2$ in which $R_1$ represents a linear or branched fatty acid residue containing from 4 to 40 carbon atoms and $R_2$ represents a hydrocarbon chain that is especially branched, containing from 4 to 40 carbon atoms, provided that $R_1+R_2 \geq 16$, for instance Purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or di(2-ethylhexyl) succinate; preferably, $R_1$ represents a linear or branched fatty acid residue comprising from 4 to 40 carbon atoms and $R_2$ represents a hydrocarbon chain, which is especially branched, containing from 4 to 40 carbon atoms and are such that $R_1$ and $R_2 \geq 20$, linear fatty acid esters with a total carbon number ranging from 35 to 70, for instance pentaerythrityl tetrapelargonate (MW=697 g/mol), hydroxylated esters, preferably with a total carbon number ranging from 35 to 70, for instance polyglyceryl-2 triisostearate (MW=965 g/mol), isostearyl lactate, octyl hydroxystearate, octyldodecyl hydroxystearate, diisostearyl malate, glyceryl stearate; diethylene glycol diisononanoate, esters of aromatic acids and of alcohols comprising 4 to 22 atoms, such as tridecyl trimellitate (MW=757 g/mol), esters of branched $C_{24}$-$C_{28}$ fatty alcohols or fatty acids such as those described in Application EP-A-0 955 039, and especially triisoarachidyl citrate (MW=1033.76 g/mol), pentaerythrityl tetraisononanoate (MW=697 g/mol), glyceryl triisostearate (MM=891 g/mol), glyceryl tri(2-decyltetradecanoate) (MW=1143 g/mol), pentaerythrityl tetraisostearate (MW=1202 g/mol), polyglyceryl-2 tetraisostearate (MW=1232 g/mol) or pentaerythrityl tetra(2-decyltetradecanoate) (MW=1538 g/mol), polyesters resulting from the esterification of at least one hydroxylated carboxylic acid triglyceride with an aliphatic monocarboxylic acid and with an aliphatic dicarboxylic acid, which is optionally unsaturated, for instance the succinic acid and isostearic acid castor oil sold under the reference Zenigloss by Zenitech, esters of a diol dimer and of a diacid dimer of general formula HO—$R^1$—(—OCO—$R^2$—COO—$R^1$—)$_h$—OH, in which:

$R^1$ represents a diol dimer residue obtained by hydrogenation of dilinoleic diacid, $R^2$ represents a hydrogenated dilinoleic diacid residue, and h represents an integer ranging from 1 to 9, especially the esters of dilinoleic diacids and of dilinoleyl diol dimers sold by the company Nippon Fine Chemical under the trade names Lusplan DD-DA5® and DD-DA7®, polyesters obtained by condensation of an unsaturated fatty acid dimer and/or trimer and of diol, such as those described in Patent Application FR 0 853 634, in particular such as dilinoleic acid and 1,4-butanediol. Mention may especially be made in this respect of the polymer sold by Biosynthis under the name Viscoplast 14436H (INCI name: Dilinoleic Acid/Butanediol Copolymer), or copolymers of polyols and of diacid dimers, and esters thereof, such as Hailuscent ISDA, fatty alcohols containing from 12 to 26 carbon atoms, which are preferably branched, for instance octyldodecanol, 2-butyloctanol, 2-hexyldecanol, 2-undecylpentadecanol and oleyl alcohol, $C_{12}$-$C_{22}$ higher fatty acids, such as oleic acid, linoleic acid, linolenic acid, and mixtures thereof, oils of vegetable origin, such as sesame oil (820.6 g/mol), fatty acids containing from 12 to 26 carbon atoms, for instance oleic acid, dialkyl carbonates, the two alkyl chains possibly being identical or different, such as dicaprylyl carbonate sold under the name Cetiol CC® by Cognis, vinylpyrrolidone copolymers such as the vinylpyrrolidone/1-hexadecene copolymer, Antaron V-216, sold or manufactured by the company ISP (MW=7300 g/mol), and mixtures thereof.

According to a particular embodiment, a composition in accordance with the invention comprises at least one vinylpyrrolidone/1-hexadecene copolymer.

Preferably, the composition according to the invention comprises at least one non-volatile oil, preferably a hydrocarbon ester oil, preferably chosen from:

synthetic esters of formula $R_1COOR_2$ in which $R_1$ represents a linear or branched fatty acid residue containing from 4 to 40 carbon atoms and $R_2$ represents a hydrocarbon chain that is especially branched, containing from 4 to 40 carbon atoms, provided that $R_1+R_2 \geq 16$, preferably chosen from Purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or di(2-ethylhexyl) succinate;

esters of aromatic acids and of alcohols comprising 4 to 22 atoms, such as tridecyl trimellitate (MW=757 g/mol);

and mixtures thereof.

Preferably, the composition according to the invention comprises at least one second oil chosen from synthetic esters of formula $R_1COOR_2$ in which $R_1$ represents a linear or branched fatty acid residue containing from 4 to 40 carbon atoms and $R_2$ represents a hydrocarbon chain that is especially branched, containing from 4 to 40 carbon atoms, provided that $R_1+R_2 \geq 16$.

Preferably, the composition according to the invention comprises at least one non-volatile hydrocarbon ester oil (that is to say, comprising at least one ester functional group), preferably chosen from isostearyl isostearate, and/or diisostearyl malate, and/or tridecyl trimellitate and their mixtures.

According to a preferred embodiment, a composition in accordance with the invention comprises isostearyl isostearate.

According to a preferred embodiment, a composition in accordance with the invention comprises diisostearyl malate.

According to a preferred embodiment, a composition in accordance with the invention comprises tridecyl trimellitate.

According to another embodiment, the non-volatile polar oil may be a fluoro oil.

The fluoro oils that may be used according to the invention may be chosen from fluorosilicone oils, fluoro polyethers and fluorosilicones as described in document EP-A-847 752, and perfluoro compounds.

According to the invention, the term "perfluoro compounds" means compounds in which all the hydrogen atoms have been replaced with fluorine atoms.

According to a preferred embodiment, the fluoro oil according to the invention is chosen from perfluoro oils.

As examples of perfluoro oils that may be used in the invention, mention may be made of perfluorodecalins and perfluoroperhydrophenanthrenes.

According to a preferred embodiment, the fluoro oil is chosen from perfluoroperhydrophenanthrenes, and especially the Fiflow® products sold by the company Créations Couleurs. In particular, use may be made of the fluoro oil for which the INCI name is Perfluoroperhydrophenanthrene, sold under the reference Fiflow 220 by the company F2 Chemicals.

According to another embodiment, the non-volatile polar oil may be a silicone oil.

The non-volatile silicone oil that may be used in the invention may be chosen especially from silicone oils especially with a viscosity at 25° C. of greater than or equal to 9 centistokes (cSt) ($9\times10^{-6}$ m$^2$/s) and less than 800 000 cSt, preferably between 50 and 600 000 cSt and preferably between 100 and 500 000 cSt. The viscosity of this silicone oil may be measured according to Standard ASTM D-445.

In particular, the non-volatile silicone oil may be chosen from:
  non-volatile linear or branched polydimethylsiloxanes (PDMSs);
  polydimethylsiloxanes comprising alkyl, alkoxy or phenyl groups, which are pendent or at the end of the silicone chain, these groups containing from 2 to 24 carbon atoms; and
  phenyl silicone oils, in particular chosen from:
  phenyl trimethicones, especially such as Phenyl Trimethylsiloxy Trisiloxane, sold especially under the reference Dow Corning 556 Cosmetic Grade Fluid,
  phenyl dimethicones,
  phenyl trimethylsiloxy diphenylsiloxanes,
  diphenyl dimethicones,
  diphenyl methyldiphenyl trisiloxanes,
  2-phenylethyl trimethylsiloxysilicates,
  trimethyl pentaphenyl trisiloxanes, especially such as the silicone oil sold by Dow Corning under the reference PH-1555 HRI or Dow Corning 555 Cosmetic Fluid (chemical name: 1,3,5-trimethyl-1,1,3,5,5-pentaphenyl trisiloxane; INCI name: Trimethyl Pentaphenyl Trisiloxane),
  trimethyl siloxyphenyl dimethicones, especially such as the product sold under the reference Belsil PDM 1000 by the company Wacker.

According to a preferred embodiment, the composition according to the invention comprises at least one non-volatile silicone oil, preferably a phenyl silicone oil.

Preferably, the non-volatile oils are present in a composition according to the invention in a total content varying from 10% to 70% by weight, especially from 15% to 60% by weight and in particular from 20% to 50% by weight relative to the total weight of the composition.

Preferably, the non-volatile hydrocarbon oils are present in a composition according to the invention in a total content varying from 10% to 70% by weight, especially from 12% to 60% by weight and in particular from 15% to 50% by weight relative to the total weight of the composition.

Preferably, the non-volatile silicone oils are present in a composition according to the invention in a total content varying from 2% to 70% by weight, especially from 5% to 60% by weight and in particular from 5% to 50% by weight relative to the total weight of the composition.

Preferably, the composition according to the invention comprises a non-volatile silicone oil and a non-volatile hydrocarbon oil as second oil.

Pasty Fatty Substances

The composition according to the invention preferably comprises, in addition to the wax, at least one solid fatty substance chosen from pasty fatty substances.

Within the meaning of the present invention, the term "pasty fatty substance" is intended to denote a lipophilic fatty compound that undergoes a reversible solid/liquid change in state, that exhibits an anisotropic crystal organization in the solid state, and that comprises, at a temperature of 23° C., a liquid fraction and a solid fraction.

In other words, the starting melting point of the pasty fatty substance can be less than 23° C. The liquid fraction of the pasty fatty substance measured at 23° C. can represent from 9% to 97% by weight of the pasty fatty substance. This liquid fraction at 23° C. preferably represents between 15% and 85% and more preferably between 40% and 85% by weight.

Within the meaning of the invention, the melting point corresponds to the temperature of the most endothermic peak observed on thermal analysis (DSC) as described in Standard ISO 11357-3; 1999. The melting point of a pasty fatty substance may be measured using a differential scanning calorimeter (DSC), for example the calorimeter sold under the name MDSC 2920 by the company TA Instruments.

The measuring protocol is as follows:

A sample of 5 mg of pasty fatty substance placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of pasty fatty substance is measured as a function of the temperature. The melting point of the pasty fatty substance is the value of the temperature corresponding to the tip of the peak of the curve representing the variation in the difference in power absorbed as a function of the temperature.

The liquid fraction by weight of the pasty fatty substance at 23° C. is equal to the ratio of the enthalpy of fusion consumed at 23° C. to the enthalpy of fusion of the pasty fatty substance.

The enthalpy of fusion of the pasty fatty substance is the enthalpy consumed by the latter in order to pass from the solid state to the liquid state. The pasty fatty substance is said to be in the solid state when all of its mass is in crystalline solid form. The pasty fatty substance is said to be in the liquid state when all of its mass is in liquid form.

The enthalpy of fusion of the pasty fatty substance is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to Standard ISO 11357-3; 1999.

The enthalpy of fusion of the pasty fatty substance is the amount of energy required to make the pasty fatty substance change from the solid state to the liquid state. It is expressed in J/g.

The enthalpy of fusion consumed at 23° C. is the amount of energy absorbed by the sample to change from the solid state to the state that it has at 23° C., composed of a liquid fraction and a solid fraction.

The liquid fraction of the pasty fatty substance measured at 32° C. preferably represents from 30% to 100% by weight of the pasty fatty substance, preferably from 50% to 100%, more preferably from 60% to 100% by weight of the pasty fatty substance. When the liquid fraction of the pasty fatty substance measured at 32° C. is equal to 100%, the temperature of the end of the melting range of the pasty fatty substance is less than or equal to 32° C.

The liquid fraction of the pasty fatty substance measured at 32° C. is equal to the ratio of the enthalpy of fusion consumed at 32° C. to the enthalpy of fusion of the pasty fatty substance. The enthalpy of fusion consumed at 32° C. is calculated in the same way as the enthalpy of fusion consumed at 23° C.

The pasty fatty substance may in particular be chosen from synthetic fatty substances and fatty substances of vegetable origin. A pasty fatty substance may be obtained by synthesis from starting materials of vegetable origin.

The pasty fatty substance may be chosen from:
lanolin and derivatives thereof,
petrolatum,
polyol ethers chosen from polyalkylene glycol pentaerythrityl ethers, fatty alcohol ethers of sugars, and mixtures thereof, the polyethylene glycol pentaerythrityl ether comprising five oxyethylene (5 OE) units (CTFA name: PEG-5 Pentaerythrityl Ether), the polypropylene glycol pentaerythrityl ether comprising five oxypropylene (5 OP) units (CTFA name: PPG-5 Pentaerythrityl Ether), and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil,
polymeric or non-polymeric silicone compounds,
polymeric or non-polymeric fluoro compounds,
vinyl polymers, especially:
  olefin homopolymers and copolymers,
  hydrogenated diene homopolymers and copolymers,
  linear or branched oligomers which are homopolymers or copolymers of alkyl (meth)acrylates preferably containing a $C_8$-$C_{30}$ alkyl group,
  oligomers which are homopolymers and copolymers of vinyl esters containing $C_8$-$C_{30}$ alkyl groups, and
  oligomers which are homopolymers and copolymers of vinyl ethers containing $C_8$-$C_{30}$ alkyl groups,
  fat-soluble polyethers resulting from the polyetherification between one or more $C_2$-$C_{100}$ and preferably $C_2$-$C_{50}$ diols,
esters,
and/or mixtures thereof.

Among the fat-soluble polyethers that are particularly considered are copolymers of ethylene oxide and/or of propylene oxide with long-chain $C_6$-$C_{30}$ alkylene oxides, more preferably such that the weight ratio of the ethylene oxide and/or propylene oxide to alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially considered:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, isostearic acid and 12-hydroxystearic acid, such as, for example, bis-diglyceryl polyacyladipate-2 sold under the reference Softisan® 649 by the company Sasol,
vinyl ester homopolymers containing $C_8$-$C_{30}$ alkyl groups, such as polyvinyl laurate (sold especially under the reference Mexomer PP by the company Chimex),
the arachidyl propionate sold under the brand name Waxenol 801 by Alzo,
phytosterol esters,
fatty acid triglycerides and derivatives thereof,
pentaerythritol esters,
esters of a diol dimer and of a diacid dimer, where appropriate esterified on their free alcohol or acid functional group(s) with acid or alcohol radicals, especially dimer dilinoleate esters; such esters may be chosen especially from the esters having the following INCI nomenclature: Bis-Behenyl/Isostearyl/Phytosteryl Dimer Dilinoleyl Dimer Dilinoleate (Plandool G), Phytosteryl/Isostearyl/Cetyl/Stearyl/Behenyl Dimer Dilinoleate (Plandool H or Plandool S), and mixtures thereof,
mango butter, such as the product sold under the reference Lipex 203 by the company AarhusKarlshamn,
hydrogenated soybean oil, hydrogenated coconut oil, hydrogenated rape seed oil, mixtures of hydrogenated vegetable oils such as the mixture of hydrogenated soybean, coconut, palm and rape seed vegetable oil, for example the mixture sold under the reference Akogel® by the company AarhusKarlshamn (INCI name: Hydrogenated Vegetable Oil),
shea butter, in particular the product for which the INCI name is Butyrospermum Parkii Butter, such as the product sold under the reference Sheasoft® by the company AarhusKarlshamn,
and mixtures thereof.

According to a preferred embodiment, the pasty fatty substance is chosen from esters and in particular diglycerol esters, and their mixtures.

The choice will preferably be made, among the pasty compounds, of bis-behenyl/isostearyl/phytosteryl dimer dilinoleyl dimer dilinoleate, bis-diglyceryl polyacyladipate-2, hydrogenated castor oil, for example Risocast-DA-L sold by Kokyu Alcohol Kogyo, hydrogenated castor oil isostearate, for example Salacos HCIS (V-L) sold by Nisshin Oil, polyvinyl laurate, mango butter, shea butter, hydrogenated soybean oil, hydrogenated coconut oil, hydrogenated rape seed oil, vinylpyrrolidone/eicosene copolymers, or their mixture.

According to another embodiment, the composition is devoid of pasty fatty substances.

Preferably, the composition according to the invention comprises a content of pasty fatty substances ranging from 1% to 50% by weight, in particular ranging from 5% to 45% by weight, and especially ranging from 10% to 40% by weight, relative to the total weight of the composition.

Colourant

Preferably, the composition in accordance with the present invention comprises at least one colourant (also known as "colouring agent") which can in particular be chosen from water-soluble or fat-soluble colourants, pigments, organic lakes, pearlescent agents, materials having an optical effect, and their mixtures.

The additional colourants (other than the said lake) can be present in a content of between 0.01% and 25% by weight, preferably between 0.1% and 20% by weight, relative to the total weight of the composition.

In particular, the composition according to the invention may comprise one or more colourants chosen from water-soluble dyes and pulverulent colourants, for instance pigments, organic lakes, pearlescent agents and glitter, well known to those skilled in the art.

The term "pigments" should be understood as meaning white or coloured and inorganic or organic particles which are insoluble in an aqueous solution and which are intended to colour and/or opacify the resulting film.

The pigments may be present in a proportion of from 0.01% to 20% by weight, especially from 0.1% to 15% by weight and in particular from 0.2% to 10% by weight, relative to the total weight of the cosmetic composition.

As inorganic pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The colourant may also comprise a pigment with a structure that may be, for example, of silica microspheres containing iron oxide type. An example of a pigment having this structure is the product sold by the company Miyoshi under the reference PC Ball PC-LL-100 P, this pigment being composed of silica microspheres containing yellow iron oxide.

Among the organic pigments that may be used in the invention, mention may be made of carbon black, pigments of D&C type, or alternatively the diketopyrrolopyrroles (DPPs) described in documents EP-A-542 669, EP-A-787 730, EP-A-787 731 and WO-A-96/08537.

Organic Lake

Preferably, a composition according to the invention comprises at least one organic lake.

Organic lakes are organic pigments formed from a dye attached to a substrate.

The term "pigments" should be understood as meaning white or coloured and inorganic or organic particles which are insoluble in an aqueous solution and which are intended to colour and/or opacify the resulting film.

Organic lakes, which are also known as organic pigments, may be chosen from the materials below, and mixtures thereof:

cochineal carmine;

organic pigments of azo dyes, anthraquinone dyes, indigoid dyes, xanthene dyes, pyrene dyes, quinoline dyes, triphenylmethane dyes and fluoran dyes. Among the organic pigments that may especially be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6;

insoluble sodium, potassium, calcium, barium, aluminium, zirconium, strontium or titanium salts of acid dyes such as azo, anthraquinone, indigoid, xanthene, pyrene, quinoline, triphenylmethane or fluoran dyes, these dyes possibly comprising at least one carboxylic or sulphonic acid group.

The organic lakes may also be supported on an organic support such as rosin or aluminium benzoate, for example.

Among the organic lakes, mention may in particular be made of those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake.

The chemical materials corresponding to each of the organic colourants cited previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

According to a preferred embodiment, the organic lake(s) are chosen from cochineal carmine and insoluble sodium, potassium, calcium, barium, aluminium, zirconium, strontium or titanium salts of acid dyes such as azo, anthraquinone, indigoid, xanthene, pyrene, quinoline, triphenylmethane or fluoran dyes, these dyes possibly comprising at least one carboxylic or sulphonic acid group.

The organic lakes may be present in a proportion of from 0.01% to 20% by weight, especially from 0.01% to 15% by weight and in particular from 0.02% to 10% by weight, relative to the total weight of the composition.

The term "pearlescent agents" should be understood as meaning coloured particles of any form, which may or may not be iridescent, especially produced by certain molluscs in their shells, or alternatively synthesized, and which have a colour effect via optical interference.

The pearlescent agents may be chosen from pearlescent pigments such as titanium mica coated with an iron oxide, titanium mica coated with bismuth oxychloride, titanium mica coated with chromium oxide, titanium mica coated with an organic dye and also pearlescent pigments based on bismuth oxychloride. They may also be mica particles at the surface of which are superimposed at least two successive layers of metal oxides and/or of organic colourants.

Examples of pearlescent agents that may also be mentioned include natural mica coated with titanium oxide, with iron oxide, with natural pigment or with bismuth oxychloride.

Among the pearlescent agents available on the market, mention may be made of the pearlescent agents Timica, Flamenco and Duochrome (based on mica) sold by the company Engelhard, the Timiron pearlescent agents sold by the company Merck, the Prestige mica-based pearlescent agents sold by the company Eckart, and the Sunshine synthetic mica-based pearlescent agents sold by the company Sun Chemical.

The pearlescent agents may more particularly have a yellow, pink, red, bronze, orange, brown, gold and/or coppery colour or glint.

As illustrations of pearlescent agents that may be used in the context of the present invention, mention may in particular be made of gold-coloured pearlescent agents sold especially by the company Engelhard under the names Brilliant gold 212G (Timica), Gold 222C (Cloisonne), Sparkle gold (Timica), Gold 4504 (Chromalite) and Monarch gold 233X (Cloisonne); the bronze pearlescent agents sold especially by the company Merck under the names Bronze fine (17384) (Colorona) and Bronze (17353) (Colorona) and by the company Engelhard under the name Super bronze (Cloisonne); the orange pearlescent agents sold especially by the company Engelhard under the names Orange 363C (Cloisonne) and Orange MCR 101 (Cosmica) and by the company Merck under the names Passion orange (Colorona) and Matte orange (17449) (Microna); the brown-tinted pearlescent agents sold especially by the company Engelhard under the names Nu-antique copper 340XB (Cloisonne) and Brown CL4509 (Chromalite); the pearlescent agents with a copper glint sold especially by the company Engelhard under the name Copper 340A (Timica); the pearlescent agents with a red glint sold especially by the company Merck under the name Sienna fine (17386) (Colorona); the pearlescent agents with a yellow glint sold especially by the company Engelhard under the name Yellow (4502) (Chromalite); the red-tinted pearlescent agents with a golden glint sold especially by the company Engelhard under the name Sunstone G012 (Gemtone); the pink pearlescent agents sold especially by the company Engelhard under the name Tan opale G005 (Gemtone); the black pearlescent agents with a golden glint sold especially by the company Engelhard under the name Nu antique bronze 240 AB (Timica); the blue pearlescent agents sold especially by the company Merck under the name Matte blue (17433) (Microna); the white pearlescent agents with a silvery glint sold especially by the company Merck under the name Xirona Silver; and the golden-green pinkish-orange pearlescent agents sold especially by the company Merck under the name Indian summer (Xirona), and mixtures thereof.

The term "dyes" should be understood as meaning compounds, generally organic compounds, which are soluble in fatty substances such as oils or in an aqueous-alcoholic phase.

The cosmetic composition according to the invention may also comprise water-soluble or fat-soluble dyes. The fat-soluble dyes are, for example, Sudan red, DC Red 17, DC Green 6, β-carotene, Sudan brown, DC Yellow 11, DC Violet 2, DC Orange 5 and quinoline yellow.

The water-soluble dyes are, for example, beetroot juice and methylene blue.

The cosmetic composition according to the invention may also contain at least one material with a specific optical effect.

This effect is different from a simple conventional hue effect, i.e. a unified and stabilized effect as produced by standard colourants, for instance monochromatic pigments.

Within the meaning of the invention, the term "stabilized" means lacking an effect of variability in the colour as a function of the angle of observation or alternatively in response to a temperature change.

For example, this material may be chosen from particles with a metallic glint, goniochromatic colouring agents, diffractive pigments, thermochromic agents, optical brighteners, and also fibres, especially interference fibres. Needless to say, these various materials may be combined so as to afford the simultaneous manifestation of two effects, indeed even of a novel effect in accordance with the invention.

Fillers

Preferably, a composition according to the invention also contains at least one or more filler(s).

The term "fillers" should be understood as meaning colourless or white and inorganic or synthetic particles of any shape which are insoluble in the medium of the composition, irrespective of the temperature at which the composition is manufactured.

These fillers serve especially to modify the rheology or the texture of the composition.

The fillers may be inorganic or organic and of any shape, platelet, spherical or oblong, irrespective of the crystallographic form (for example sheet, cubic, hexagonal, orthorhombic, etc.).

Mention may be made of talc, mica, silica, kaolin, bentone, fumed silica particles that have optionally been hydrophilically or hydrophobically treated, polyamide (Nylon®) powder (Orgasol® from Atochem, SP-500 from Toray (Dow Corning)), poly-β-alanine powder and polyethylene powder, tetrafluoroethylene polymer (Teflon®) powders, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning) and silicone resin microbeads (for example Tospearls® from Toshiba), precipitated calcium carbonate, magnesium carbonate, basic magnesium carbonate, hydroxyapatite, hollow silica microspheres (Silica Beads® from Maprecos), elastomeric polyorganosiloxane particles, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

They may also be particles comprising a copolymer, the said copolymer comprising trimethylol hexyllactone. In particular, it may be a hexamethylene diisocyanate/trimethylol hexyllactone copolymer.

Such particles are especially commercially available, for example, under the name Plastic Powder D-400® or Plastic Powder D-800® from the company Toshiki.

According to a preferred embodiment, the composition comprises at least one filler chosen in particular from kaolin, polyamide powders, copolymers comprising trimethylol hexyllactone, preferably a hexamethylene diisocyanate/trimethylol hexyllactone copolymer, and/or fumed silica particles that have optionally been hydrophilically or hydrophobically treated, preferably hydrophobically treated, and mixture thereof.

According to a preferred embodiment, the composition comprises at least one filler chosen from kaolin, polyamide powders, and/or copolymers comprising trimethylol hexyllactone, preferably a hexamethylene diisocyanate/trimethylol hexyllactone copolymer, and mixture thereof.

Preferably, the composition comprises at least one filler known as Silica Dimethyl Silylate (according to the CTFA).

The hydrophobic groups may especially be dimethylsilyloxyl or polydimethylsiloxane groups, which are especially obtained by treating fumed silica in the presence of polydimethylsiloxane or dimethyldichlorosilane. Silicas thus treated are known as Silica Dimethyl Silylate according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

According to a preferred embodiment, the composition comprises:
- at least one first filler chosen from copolymers comprising trimethylol hexyllactone, preferably a hexamethylene diisocyanate/trimethylol hexyllactone copolymer, and hydrophobically treated fumed silica filler and
- at least one second filler chosen from kaolin and polyamide powders.

According to a particularly preferred embodiment, the composition according to the invention comprises at least particles comprising a copolymer, the said copolymer comprising trimethylol hexyllactone. According to a particularly preferred embodiment, the composition according to the invention comprises a hexamethylene diisocyanate/trimethylol hexyllactone copolymer.

Preferably, the composition according to the invention is devoid of fumed silica particles, in particular of silica particles having a nanometric size.

Preferably, the composition according to the invention is devoid of filler referred to as Silica Dimethyl Silylate.

The term "devoid" of fumed silica particles especially means that this compound is not deliberately added to the compositions, but may be present in trace amounts in the various compounds used in the compositions.

Preferably, the composition according to the invention comprises a total content of filler(s) ranging from 1% to 20% by weight and preferably from 2% to 15% by weight, relative to the total weight of the composition.

Preferably, the composition according to the invention comprises a total content of filler(s) ranging from 5% to 12% by weight, relative to the total weight of the composition.

Preferably, the composition according to the invention comprises a total content of particles of copolymer comprising trimethylol hexyllactone ranging from 1% to 20%, preferably from 2% to 15% by weight, preferably ranging from 2% to 12%, preferably ranging from 2% to 10% by weight, relative to the total weight of the composition.

Usual Additional Cosmetic Ingredients

A composition according to the invention may also comprise any usual cosmetic ingredient, which may be chosen especially from antioxidants, fragrances, preservatives, neutralizing agents, surfactants, sunscreens, sweeteners, vitamins, moisturizing agents, emollients, hydrophilic or lipophilic active agents, agents for combating free radicals, sequestering agents, and mixtures thereof.

Needless to say, a person skilled in the art will take care to select the optional additional ingredients and/or the amounts thereof such that the advantageous properties of the composition according to the invention are not, or are not substantially, adversely affected by the envisioned addition.

Preferably, the composition according to the invention is a lip product such as a lip gloss, or a lipcare product.

The invention is illustrated in greater detail by the examples described below, which are given as non-limiting illustrations.

The percentages are weight percentages.

In the examples that follow, the weight percentages are indicated relative to the total weight of the composition.

The weight percentages are shown as starting material.

Examples 1 and 2: Liquid Lipsticks

The following liquid lipstick (gloss) compositions 1 and 2 were prepared:

| Compounds | Composition 1 according to the invention (% by weight) | Composition 2 according to the invention (% by weight) |
|---|---|---|
| BHT | 0.03 | 0.03 |
| Kaolin | 5 | 5 |
| Silica Dimethyl Silylate (Aerosil ® R 972 from Evonik Degussa) | 2 | 2 |
| Red 7 lake | 3.83 | 3.83 |
| Red 28 lake | 1.17 | 1.17 |
| Iron oxides | 1 | 1 |
| Bis-Diglyceryl Polyacyladipate-2 (Softisan ® 649 from Sasol) | q.s. for 100 | q.s. for 100 |
| Isostearyl isostearate | 3.9 | 3.9 |
| Tridecyl trimellitate | 7.3 | 7.3 |
| Ozokerite (Ozokerite Wax Pastilles SP 1021 P from Strahl & Pitsch) | — | 1.3 |
| Hydrogenated polyisobutene (Parleam ® from Nof Corporation) | 8.6 | 8.6 |
| Polyethylene (Asensa ® SC 211 from Honeywell) | 1.2 | 1.2 |
| Polyethylene (Performalene 500-L Polyethylene from New Phase Technologies) | 1 | — |
| Nylon-12 (SP - 500 from Toray (Dow Corning)) | 1.5 | 1.5 |
| Phenyl Trimethicone (Dow Corning 556 Cosmetic Grade Fluid from Dow Corning) | 7.8 | 7.8 |
| Vinyl Dimethicone/Methicone Silsesquioxane Crosspolymer (KSP 100 from Shin Etsu) | 2 | 2 |
| Dimethicone (and) Dimethicone Crosspolymer (Dow Corning 9041 Silicone Elastomer Blend from Dow Corning) comprising 15.5% of elastomer in dimethicone | 33 | 33 |
| TOTAL | 100 | 100 |

Preparation Process

Compositions 1 and 2 were obtained according to the following protocol:

In a first stage, the fillers, pigments and/or active agents were ground in a triple roll mill in a portion of the oily phase (phenyl trimethicone, hydrogenated polyisobutene, tridecyl trimellitate, isostearyl isostearate and bis-diglyceryl polyacyladipate-2).

The remainder of the fat-soluble ingredients were then mixed in a heating pan at a temperature of about 100° C. with Rayneri blending until a homogeneous mixture was obtained. The ground pigmentary material was then incorporated into the mixture and stirring was continued until the mixture was homogeneous.

Finally, the composition was poured into small pots and then placed at ambient temperature for 24 h.

Viscosity

The viscosity of composition 1 at 20° C. was evaluated according to the protocol described previously, and is of the order of 12.5 Pa·s.

The viscosity of composition 2 at 20° C. was evaluated according to the protocol described previously, and is of the order of 13 Pa·s.

Evaluation of the Compositions

Compositions 1 and 2 according to the invention are easy to apply and make it possible to obtain a deposited layer on the lips which is homogeneous, matt (non-glossy) and non-tacky and which confers, on the lips, a "velvet" feeling, that is to say a soft and velvety feeling, without a feeling of dryness or tightness.

Examples 3 to 6: Liquid Lipsticks

The following liquid lipstick (gloss) compositions 3 to 6 were prepared. Compositions 3 and 4 illustrate the invention and compositions 5 and 6 are comparative compositions outside the invention as the ratio by weight on a dry basis of organopolysiloxane elastomer conveyed in an oil/organopolysiloxane elastomer powder coated with a silicone resin is less than 2.

| Compounds | Composition 3 according to the invention (% by weight) | Composition 4 according to the invention (% by weight) | Comparative composition 5 outside the invention (% by weight) | Comparative composition 6 outside the invention (% by weight) |
|---|---|---|---|---|
| Kaolin | 4 | 4 | 4 | 4 |
| HDI/Trimethylol Hexyllactone Crosspolymer (Plastic Powder D 400 from Toshiki Pigment) | 4 | — | 4 | 4 |
| Silica Dimethyl Silylate (Aerosil ® R 972 from Evonik Degussa) | — | 4 | — | — |
| Bis-Diglyceryl Polyacyladipate-2 (Softisan ® 649 from Sasol) | q.s. for 100 | q.s. for 100 | q.s. for 100 | q.s. for 100 |
| Isostearyl isostearate | 3.3 | 3.3 | 3.3 | 3.3 |
| Diisostearyl malate | 7.7 | 7.7 | 7.7 | 7.7 |
| Hydrogenated polyisobutene (Parleam ® from Nof Corporation) | 7.2 | 7.2 | 7.2 | 7.2 |
| Polyethylene (Asensa ® SC 211 from Honeywell) | 1.2 | 1.2 | 1.2 | 1.2 |
| Polyethylene (Performalene 500-L Polyethylene from New Phase Technologies) | 1 | 1 | 1 | 1 |
| Nylon-12 (SP - 500 from Toray (Dow Corning)) | 1.5 | 1.5 | 1.5 | 1.5 |
| Phenyl Trimethicone (Dow Corning 556 Cosmetic Grade Fluid from Dow Corning) | 4.9 | 4.9 | 4.9 | 4.9 |
| Vinyl Dimethicone/Methicone Silsesquioxane Crosspolymer (KSP 100 from Shin Etsu) | 2 | 2 | 2 | 2 |
| Dimethicone (and) Dimethicone Crosspolymer (Dow Corning 9041 Silicone Elastomer Blend from Dow Corning) comprising 15.5% of elastomer in Dimethicone 5 cSt oil | 37 | 37 | 18.71 | 37 |
| Dimethicone 5 cSt (Xiameter PMX-200 Silicone Fluid 5 cSt from Dow Corning) | — | — | 18.29 | 15.49 |
| Dimethicone/Vinyl Dimethicone Crosspolymer (DC9506 from Dow Corning) (organopolysiloxane elastomer powder) | — | — | — | 2.8 |
| Pentylene glycol | 1 | 1 | 1 | 1 |
| Caprylyl glycol | 0.5 | 0.5 | 0.5 | 0.5 |
| Red 7 lake | 3.83 | 3.83 | 3.83 | 3.83 |
| Red 28 lake | 1.17 | 1.17 | 1.17 | 1.17 |
| Iron oxides | 1 | 1 | 1 | 1 |

| Compounds | Composition 3 according to the invention (% by weight) | Composition 4 according to the invention (% by weight) | Comparative composition 5 outside the invention (% by weight) | Comparative composition 6 outside the invention (% by weight) |
|---|---|---|---|---|
| Yellow 6 lake | 0.02 | 0.02 | 0.02 | 0.02 |
| Mica | 2 | 2 | 2 | 2 |
| TOTAL | 100 | 100 | 100 | 100 |
| Ratio on a dry basis of organopolysiloxane elastomer conveyed in an oil/organopolysiloxane elastomer powder coated with silicone resin: | 2.87 | 2.87 | 1.45 | 1.45 |
| Total content by weight of organopolysiloxane elastomer (total on a dry basis) | 7.7 | 7.7 | 4.9 | 7.7 |
| Viscosity at 20° C. (in Pa · s) | 10.5 | 33 | 3.5 | 2.5 |
| Appearance of the deposited layer on the lips | Matt | Matt | Glossy | Glossy |

Preparation Process

Compositions 3 to 6 were obtained according to the following protocol:

In a first stage, the fillers, pigments and/or active agents were ground in a triple roll mill in a portion of the oily phase (phenyl trimethicone, hydrogenated polyisobutene, diisostearyl malate, isostearyl isostearate and bis-diglyceryl polyacyladipate-2).

The remainder of the fat-soluble ingredients were then mixed in a heating pan at a temperature of about 100° C. with Rayneri blending until a homogeneous mixture was obtained. The ground pigmentary material was then incorporated into the mixture and stirring was continued until the mixture was homogeneous.

Finally, the composition was poured into small pots and then placed at ambient temperature for 24 h.

Viscosity

The viscosity at 20° C. of compositions 3 to 6 was evaluated according to the protocol described previously.

Evaluation of the Compositions

Compositions 3 and 4 according to the invention make it possible to obtain a matt deposited layer. The deposited layers obtained with compositions 3 and 4 according to the invention are non-tacky and confer, on the lips, a "velvet" feeling, that is to say a soft and velvety feeling.

Furthermore, composition 3 is easy to apply and makes it possible to obtain a homogeneous and very comfortable deposited layer on the lips (no feeling of dryness or tightness). Composition 4, the viscosity of which is greater, is thicker and spreads slightly less well during application.

On the other hand, the deposited layers on the lips obtained with comparative compositions 5 and 6 are not matt but are glossy. Nevertheless, the total content of organopolysiloxane elastomer in comparative composition 6 is the same as in compositions 3 and 4 according to the invention. These comparative compositions 5 and 6 thus do not meet the objectives of the invention.

Furthermore, comparative composition 5 is not liquid but forms a highly aerated foam.

Advantageously, the composition according to the invention comprises a total content of organopolysiloxane elastomer(s) (i.e., =of elastomer(s) conveyed in an oil or not conveyed in an oil+organopolysiloxane elastomer coated with silicone resin solids) ranging from 1% to 25% by weight, preferably from 2% to 15% by weight and more preferably still from 5% to 15% by weight, relative to the total weight of the composition.

The invention claimed is:

1. An anhydrous cosmetic composition for making up and/or caring for the skin and/or lips comprising, in a physiologically acceptable medium, a fatty phase comprising:
   an organopolysiloxane elastomer powder coated with silicone resin;
   an organopolysiloxane elastomer conveyed in a first oil;
   a wax in an amount of 0.5 to 5% by weight of the composition;
   a second oil;
   wherein
   the organopolysiloxane elastomer and the organopolysiloxane elastomer powder coated with a silicone resin are present in a ratio by weight on a dry basis of organopolysiloxane elastomer conveyed in an oil to organopolysiloxane elastomer powder coated with a silicone resin of greater than 2.5 to 1, and
   the composition is liquid at 20° C.

2. An anhydrous cosmetic composition for making up and/or caring for the skin and/or lips comprising, in a physiologically acceptable medium, a fatty phase comprising:
   an organopolysiloxane elastomer powder coated with silicone resin;
   an organopolysiloxane elastomer conveyed in a first oil;
   a wax in an amount of 0.5 to 5% by weight of the composition;
   a second oil;
   wherein the organopolysiloxane elastomer and the organopolysiloxane elastomer powder coated with a silicone resin are present in a ratio by weight on a dry basis of organopolysiloxane elastomer conveyed in an oil to organopolysiloxane elastomer powder coated with a silicone resin of greater than 2.5 to 1,
   wherein the composition is liquid at 20° C.,
   with the exception that the composition is not the following liquid lipstick compositions 1 and 2:

| Compounds | Composition 1 (% by weight) | Composition 2 (% by weight) |
| --- | --- | --- |
| BHT | 0.03 | 0.03 |
| Kaolin | 5 | 5 |
| Silica Dimethyl Silylate (Aerosil ® R 972 from Evonik Degussa) | 2 | 2 |
| Red 7 lake | 3.83 | 3.83 |
| Red 28 lake | 1.17 | 1.17 |
| Iron oxides | 1 | 1 |
| Bis-Diglyceryl Polyacyladipate-2 (Softisan ® 649 from Sasol) | q.s. for 100 | q.s. for 100 |
| Isostearyl isostearate | 3.9 | 3.9 |
| Tridecyl trimellitate | 7.3 | 7.3 |
| Ozokerite (Ozokerite Wax Pastilles SP 1021 P from Strahl & Pitsch) | — | 1.3 |
| Hydrogenated polyisobutene (Parleam ® from Nof Corporation) | 8.6 | 8.6 |
| Polyethylene (Asensa ® SC 211 from Honeywell) | 1.2 | 1.2 |
| Polyethylene (Performalene 500-L Polyethylene from New Phase Technologies) | 1 | — |
| Nylon-12 (SP - 500 from Toray (Dow Corning)) | 1.5 | 1.5 |
| Phenyl Trimethicone (Dow Corning 556 Cosmetic Grade Fluid from Dow Corning) | 7.8 | 7.8 |
| Vinyl Dimethicone/Methicone Silsesquioxane Crosspolymer (KSP 100 from Shin Etsu) | 2 | 2 |
| Dimethicone (and) Dimethicone Crosspolymer (Dow Corning 9041 Silicone Elastomer Blend from Dow Corning) comprising 15.5% of elastomer in dimethicone | 33 | 33 |
| TOTAL | 100 | 100. |

3. The anhydrous cosmetic composition of claim 1, wherein the organopolysiloxane elastomer powder is coated with silsesquioxane resin.

4. The anhydrous cosmetic composition of claim 1, wherein the organopolysiloxane elastomer powder coated with silicone resin is present in a content ranging from 0.5% to 20% by weight, relative to the total weight of the composition.

5. The anhydrous cosmetic composition of claim 1, wherein the organopolysiloxane elastomer is conveyed in the first oil, which is a non-volatile oil in the form of an organopolysiloxane elastomer gel.

6. The anhydrous cosmetic composition of claim 1, wherein the organopolysiloxane elastomer conveyed in a first oil is non-emulsifying and is devoid of a hydrophilic chain and polyoxyalkylene and polyglyceryl units.

7. The anhydrous cosmetic composition of claim 1, wherein the organopolysiloxane elastomer conveyed in an oil is present in a total solids content ranging from 0.5% to 20% by weight relative to the total weight of the composition.

8. The anhydrous cosmetic composition of claim 1, wherein the organopolysiloxane elastomer is obtained by a crosslinking addition reaction of a diorganopolysiloxane comprising at least two hydrogens each bonded to a silicon, and a diorganopolysiloxane comprising at least two ethylenically unsaturated groups bonded to silicon, in the presence of a platinum catalyst.

9. The anhydrous cosmetic composition of claim 1, wherein the organopolysiloxane elastomer and the organopolysiloxane elastomer powder coated with a silicone resin are present in a ratio by weight on a dry basis of organopolysiloxane elastomer conveyed in an oil to organopolysiloxane elastomer powder coated with a silicone resin between 2.5:1 and 10:1.

10. The anhydrous cosmetic composition of claim 1, comprising a total content of an organopolysiloxane elastomer of greater than 5% by weight relative to the total weight of the composition.

11. The anhydrous cosmetic composition of claim 1, wherein the wax is at least one non-polar hydrocarbon wax selected from the group consisting of a microcrystalline wax, a paraffin wax, ozokerite, and a polyethylene wax.

12. The anhydrous cosmetic composition of claim 1, further comprising at least one colorant selected from the group consisting of water-soluble or fat-soluble colorants, pigments, organic lakes, pearlescent agents, and materials having an optical effect.

13. The anhydrous cosmetic composition of claim 1, further comprising an organic lake, the organic lake being present in a proportion of 0.01% to 20% by weight, relative to the total weight of the composition.

14. The anhydrous cosmetic composition of claim 1, wherein the second oil is at least one selected from the group consisting of a synthetic ester of formula $R_1COOR_2$ in which $R_1$ represents a linear or branched fatty acid residue comprising 4 to 40 carbon atoms and $R_2$ represents a hydrocarbon chain comprising 4 to 40 carbon atoms, provided that $R_1+R_2 \geq 16$, an ester of an aromatic acid and an alcohol comprising 4 to 22 atoms, a silicone oil, and a hydrogenated polyisobutylene.

15. The anhydrous cosmetic composition of claim 1, further comprising at least one filler chosen from the group consisting of kaolin, a polyamide powder, a copolymer comprising trimethylol hexyllactone, and a fumed silica particle.

16. The anhydrous cosmetic composition of claim 1, further comprising at least one pasty fatty substance selected from the group consisting of bis-behenyl/isostearyl/phytosteryl dimer dilinoleyl dimer dilinoleate, bis-diglyceryl polyacyladipate-2, hydrogenated castor oil, hydrogenated castor oil isostearate, polyvinyl laurate, mango butter, shea butter, hydrogenated soybean oil, hydrogenated coconut oil, hydrogenated rape seed oil, and vinylpyrrolidone/eicosene copolymers.

17. The anhydrous cosmetic composition of claim 1, wherein the composition is a lip product or a lipcare product.

18. A cosmetic method for caring for and/or making up the skin and/or lips, comprising
applying, to the lips, the composition of claim 1.

19. The anhydrous cosmetic composition of claim 1, comprising a wax content of from 1% to 5% by weight, relative to the total weight of the composition.

20. The anhydrous cosmetic composition of claim 1, comprising a total content of an organopolysiloxane elastomer of greater than 5% by weight relative to the total weight of the composition,
wherein the wax is at least one non-polar hydrocarbon wax selected from the group consisting of a microcrystalline wax, a paraffin wax, ozokerite, and a polyethylene wax, and
wherein the second oil is at least one selected from the group consisting of a synthetic ester of formula $R_1COOR_2$ in which $R_1$ represents a linear or branched fatty acid residue comprising 4 to 40 carbon atoms and $R_2$ represents a hydrocarbon chain comprising 4 to 40 carbon atoms, provided that $R_1+R_2 \geq 16$, an ester of an aromatic acid and an alcohol comprising 4 to 22 atoms, a silicone oil, and a hydrogenated polyisobutylene.

21. The anhydrous cosmetic composition of claim 1, wherein the organopolysiloxane elastomer and the organopolysiloxane elastomer powder coated with a silicone resin are present in a ratio by weight on a dry basis of organopolysiloxane elastomer conveyed in an oil to organopolysiloxane elastomer powder coated with a silicone resin of greater than 2.8 to 1.

* * * * *